United States Patent [19]

Kosow et al.

[11] Patent Number: 5,110,907
[45] Date of Patent: May 5, 1992

[54] FACTOR VIII COMPLEX PURIFICATION USING HEPARIN AFFINITY CHROMATOGRAPHY

[75] Inventors: David P. Kosow, Monrovia; Prabir Bhattacharya, Walnut; Charles F. Sternburg, Norco, all of Calif.

[73] Assignee: Alpha Therapeutic Corporation, Los Angeles, Calif.

[21] Appl. No.: 388,254

[22] Filed: Aug. 1, 1989

[51] Int. Cl.$^5$ .................. A61K 35/14; C07K 5/20; C07K 13/00
[52] U.S. Cl. .................. 530/383; 530/381; 530/413; 530/415
[58] Field of Search .............. 530/383, 387, 413, 415, 530/381

[56] References Cited

U.S. PATENT DOCUMENTS

| | | | |
|---|---|---|---|
| 3,842,061 | 10/1974 | Andersson et al. | 260/112 |
| 3,920,625 | 11/1975 | Anderson et al. | 260/112 |
| 3,973,002 | 8/1976 | Hagan et al. | 530/383 |
| 4,096,136 | 6/1978 | Ayers et al. | 260/112 |
| 4,178,439 | 12/1979 | Ayers et al. | 536/59 |
| 4,361,509 | 11/1982 | Zimmerman et al. | 530/387 |
| 4,388,232 | 6/1983 | Eibl et al. | 260/112 |
| 4,397,841 | 8/1983 | Johnson | 424/101 |
| 4,522,751 | 6/1985 | Linnau et al. | 260/112 |
| 4,578,218 | 3/1986 | Saundry et al. | 260/112 |
| 4,637,994 | 6/1987 | Tani et al. | 502/404 |
| 4,675,385 | 6/1987 | Herring | 530/383 |
| 4,721,572 | 1/1988 | Jordan | 210/635 |
| 4,743,680 | 5/1988 | Mathews et al. | 530/383 |
| 4,795,806 | 1/1989 | Brown et al. | 530/383 |

FOREIGN PATENT DOCUMENTS 022052 7/1981 European Pat. Off. .
2080312 2/1982 United Kingdom .

OTHER PUBLICATIONS

Miletich et al., "The Synthesis of Sulfated Dextran Beads for Isolation of Human Plasma Coagulation Factors II, IX, and X", *Anal. Biochem.*, 105, 304–310 (1980).
Wickerhauser et al., "A Single-Step Method for the Isolation of Antithrombin III", *Vox. Sang.*, 47, 397–405 (1984).
Menache et al., "Coagulation Factor IX Concentrate: Method of Preparation and Assessment of Potential in Vivo Thrombogenicity in Animal Models", *Blood*, 64, 1220–1227 (1984).
Bajaj et al., "A Simplified Procedure for Purification of Human Prothrombin Factor IX and Factor X", *Preparative Biochem.*, 11, 397–414 (1981).
Andersson et al., "Purification and Characterization of Human Factor IX", *Thrombosis Res.*, 7, 451–459 (1975).
Pepper et al., "Chromatography of Human Prothrombin Complex on Dextran Sulphate Agarose", *Thrombosis Res.*, 11, 687–692 (1977).
Saundry et al., "Chromatography of vWF on Dextran Sulphate Sepharose", *Thrombosis Res.*, 48, 641–652 (1987).
Harrison et al., "Chromatography of the VIII/vWf Complex on Dextran Sulphate Sepharose", *Thrombosis Res.*, 50, 295–304 (1988).
Roberts et al., "von Willebrand Factor Binds Specifically to Sulfated Glycolipids", *J. Biol. Chem.*, 261, 3306–3309 (1986).
Hamer et al., "Human Factor VIII: Purification from Commercial Factor VIII Concentrate, Characterization, Identification and Radiolabeling", *Biochem. et Biophys. Acta*, 873, 356–366 (1986).
Madaras et al., "Isolation and Insolubilization of Human F VIII by Affinity Chromatography", *Haemostasis*, 7, 321–331 (1978).
Suzuki et al., "Inhibition of Factor VIII–Associated Platelet Aggregation by Heparin and Dextran Sulfate and Its Mechanism", *Biochem. et. Biophys. Acta*, 585, 416–426 (1979).
Bockenstedt et al., "Structural Basis of von Willebrand Factor Binding to Platelet Glycoprotein Ib and Collagen", *J. Clin. Invest.*, 77, 743–749 (1986).
Andersson, "Purification and Studies of Components of the Haemostatic System by Affinity Chromatography", *Chromatog.*, 215, 153–164 (1981).
Roy et al., "Covalent Attachment of Heparin to Silica: Affinity Purification of Antithrombin III from Human Plasma by Heparin-Silica-Column", 2nd Circular, Preliminary Scientific Program & Registration Information, 10th·Int'l. Symp. on Col. Lig. Chromatography, S.F., CA 5/18–23 (1986), p. 23.
Catalog of SERVA Fine Biochemicals Inc. of Westbury, N.Y. pp. LC2–LC4 (1985).

*Primary Examiner*—Robert A. Wax
*Assistant Examiner*—Richard C. Ekstrom
*Attorney, Agent, or Firm*—Christie, Parker & Hale

[57] ABSTRACT

There is provided in accordance with the practice of this invention, a process for separating Factor VIII complex from an impure protein fraction containing Factor VIII complex. An aqueous solution of the impure protein fraction containing Factor VIII complex is applied to a heparin coupled chromatographic medium to bind the Factor VIII complex to the medium. The Factor VIII is then recovered from the heparin coupled chromatographic medium by elution with an aqueous $CaCl_2$ solution.

15 Claims, No Drawings

FACTOR VIII COMPLEX PURIFICATION USING HEPARIN AFFINITY CHROMATOGRAPHY

FIELD OF THE INVENTION

This invention relates to methods useful for separating Factor VIII complex from other protein fractions found in plasma.

BACKGROUND OF THE INVENTION

Coagulation of blood is a complex process requiring the sequential interaction of a large number of components, nearly all of which are proteins. These components include Fibrinogen, Factors II, V, VII, VIII, IX, X, XI, and XII. A lack of any of these components, or a nonfunctional component, can lead to an inability of the blood to clot when required, with the resultant excessive and life-threatening blood loss to the patient.

Hemophilia A is a common bleeding disorder caused by a deficiency or abnormality of Factor VIII. The severity of this disorder clearly demonstrates the importance of Factor VIII in the pathway of blood coagulation, even though this protein is only found in trace amounts in normal plasma. Factor VIII is present in plasma as a high-molecular-weight complex (Factor VIII complex), which includes Factor VIII:C and von Willebrand factor (Factor VIII:R or vWf). Factor VIII:C promotes blood coagulation. Factor VIII:R interacts with platelets to promote aggregation of the platelets and, when incorporated in the Factor VIII complex, acts as a stabilizer for Factor VIII:C.

The primary therapeutic use of Factor VIII has been its intravenous administration to hemophilia A patients. In severe cases, relatively high concentrations of Factor VIII are required. These high concentrations are obtained by purification and concentration of Factor VIII. However, purification often leads to instability and loss of Factor VIII:C activity because of the removal of Factor VIII:R from the Factor VIII complex during purification. Thus, the resultant purified product is a mixture of both stable Factor VIII complex and unstable Factor VIII:C, along with contaminating proteins that have not been removed, and proteins, such as albumin, which have been added to the product to stabilize the Factor VIII:C. Since these solutions contain an undesirably large portion of contaminating and stabilizing proteins, and since only Factor VIII:C is effective in treating hemophilia A patients, larger amounts of proteins have to be infused into patients than would be required if all the protein were Factor VIII:C.

Affinity chromatography has frequently been used as a method for separating a desired protein from other contaminating proteins. This method relies on a specific interaction between the desired protein and a ligand attached to the chromatographic medium. The specificity of the interaction in affinity chromatography is conferred by the unique ability of a given protein to recognize and bind to specific chemical compounds which are used as the ligands. The tremendous advantage of this method of chromatography over other methods commonly used (e.g., ion-exchange), is that only the proteins which recognize the ligand will bind to the column; thus, impurities and inactive protein may be removed from the desired protein. Elution of the specifically bound protein can be achieved in an ion-exchange manner by using solutions containing high salt or, more selectively, in an affinity manner by using a second chemical compound that is recognized by the protein. When the solution containing the second chemical compound is added, the bound protein will dissociate from the ligand and bind to the "mobile" second chemical compound in the solution and elute from the column.

Ion-exchange chromatography differs from affinity chromatography in that it relies only on ionic interactions between the protein and the chromatographic medium. Such ionic interactions are non-specific. In this case, the ligands bound to the chromatography medium contain charged groups, either negatively or positively charged, rather than a chemical compound that is specifically recognized by the protein. Elution from the ion-exchange medium is also non-specific and relies only on high salt concentrations. In ion-exchange chromatography, the salt competes for the charged groups of the chromatographic medium and the protein, resulting in elution of the protein from the chromatographic medium.

Another method that has been used for the purification of Factor VIII is the binding of the Factor VIII:R portion of the Factor VIII complex to monoclonal antibodies and the subsequent elution of the Factor VIII:C from the Factor VIII-Antibody complex. This procedure results in Factor VIII:C of very high specific activities, approximately 1500–2500 units/mg of total protein, and, therefore, high purity. (The phrase "specific activity" as used herein means units of Factor VIII:C clotting activity per milligram of protein. A "unit" is defined as the amount of Factor VIII:C in one ml of normal plasma.) However, the Factor VIII:R is dissociated from Factor VIII:C during this procedure, which results in the Factor VIII:C being unstable. To overcome the instability of Factor VIII:C, large amounts of stabilizing proteins, such as human serum albumin, are added to the purified Factor VIII:C. As has been the drawback with other purification methods (discussed above), the addition of stabilizing proteins is required, and larger amounts of proteins have to be infused into patients than would be required if all the protein were Factor VIII:C.

Currently, the methods used to purify Factor VIII result in protein preparations, i.e., Factor VIII concentrates, that have a relatively low Factor VIII specific activity due to contaminating and stabilizing proteins. When the Factor VIII concentrate has a relatively low Factor VIII:C specific activity, patients must be infused with undesirably large amounts of the extraneous protein to obtain the necessary level of Factor VIII required for effective treatment. The amount of protein needed to be infused could be drastically reduced if Factor VIII complex were the only protein contained in the infusion solutions. It is therefore desirable that there be provided an improved process for the separation of Factor VIII complex, i.e., the intact Factor VIII:C/Factor VIII:R complex, from contaminating proteins.

SUMMARY OF THE INVENTION

The present invention is directed to a process for separating Factor VIII complex from an impure protein fraction containing Factor VIII complex, for example, from a plasma fraction or from any recombinant-DNA derived materials containing Factor VIII complex. The Factor VIII complex is separated by applying the impure protein fraction to a heparin coupled chromatographic medium to thereby bind Factor VIII complex to the heparin. The Factor VIII complex is eluted from the chromatographic medium using an aqueous solution containing $CaCl_2$ as the eluting agent and, thereafter, recovering the Factor VIII complex from the eluate.

DETAILED DESCRIPTION

The process of this invention provides a simple and efficient purification method for high specific activity Factor VIII complex from an impure protein fraction. The phrase "impure protein fraction" as used herein means a solution which contains one or more proteins in addition to Factor VIII complex, where removal of these additional proteins is desired. The impure protein fraction used as the starting material for the purification of Factor VIII complex may be derived from a variety of sources, such as cryoprecipitate, or other blood plasma-derived fractions, or it may be derived by recombinant-DNA techniques.

In accordance with practice of this invention, Factor VIII complex, having a high specific Factor VIII:C activity, is provided by removing the Factor VIII complex from impurities using affinity chromatography techniques. A solution containing Factor VIII complex, i.e., the impure protein fraction, is applied to an affinity chromatographic medium which comprises a heparin ligand bound to a matrix. The Factor VIII complex binds to the heparin, while other contaminating proteins pass from the affinity chromatographic medium in the effluent. Factor VIII complex is then specifically eluted from the affinity chromatographic medium with a solution containing $CaCl_2$. Heparin and $CaCl_2$ are used in this process, since both are specifically recognized by the Factor VIII complex. Since both heparin and calcium are able to bind specifically to Factor VIII complex, they are effective ligands and eluting agents, respectively, in the affinity chromatography purification of Factor VIII complex.

Since the intact Factor VIII complex is isolated by the process of this invention, i.e., the complex of Factor VIII:C and Factor VIII:R, the addition of extraneous proteins to stabilize the Factor VIII:C activity is not required. As a result, final specific activities as high as from 30 to 60 units of Factor VIII:C/mg are obtained. These values are higher than the specific activity of from 5 to 10 units/mg that are obtained for preparations where the unstable Factor VIII:C is purified in a form that is dissociated from the Factor VIII complex. In this latter case, large amounts of extraneous proteins, such as albumin, must be added to stabilize the purified Factor VIII:C activity.

Preparation of an Impure Protein Fraction

In one exemplary embodiment of the practice of this invention, the starting material for providing the impure protein fraction containing Factor VIII complex is cryoprecipitate. The cryoprecipitate is recovered from human blood plasma that has been collected and tested according to procedures approved by the U.S. Food and Drug Administration. The plasma is frozen at a temperature of about $-20°$ C., and is subsequently thawed at 0° C. to 5° C. During the thawing process, a precipitate forms (the "cryoprecipitate") which is removed by centrifugation and recovered for further purification and concentration.

The cryoprecipitate is dissolved in a "heparin solution" which comprises distilled water containing from about 30 to 150 units of heparin per ml of water. In an exemplary embodiment, 80 units of heparin per ml of water is used. The solution is then mixed at a temperature of from about 20° C. to about 30° C. until the cryoprecipitate is completely dissolved (approximately 10 minutes) to provide a cryoprecipitate/heparin solution. Preferably, the temperature during mixing is maintained at about 30° C., and the volume of heparin solution used is from about 2 to about 10 liters per kilogram of cryoprecipitate. After the cryoprecipitate is dissolved, the pH of the cryoprecipitate/heparin solution is adjusted to about $7\pm0.1$ using, for example, 0.1M HCl, and the solution is stirred for an additional 20 to 30 minutes.

One unit of heparin is defined to mean one U.S.P. (United States Pharmacopoeia) unit. The U.S.P. unit of heparin is that quantity required to prevent 1.0 ml of citrated sheep plasma from clotting for one hour after the addition of 0.2 ml of a 1:100 calcium chloride ($CaCl_2$) solution. The term "heparin" as used herein is meant to include heparin itself and the pharmaceutically-acceptable water soluble salts of heparin, e.g., the sodium salts. A suitable example of a commercially-available heparin sodium product is U.S.P. heparin from Lyphomed Company, of Melrose Park, Ill., or from Sigma Chemical Company (Sigma No. H7005), of St. Louis, Mo.

Polyethylene glycol (PEG) powder, preferably having a molecular weight in the range of from about 2000 to about 6000 (more preferably, from about 3000 to about 4000), is then added to the cryoprecipitate/heparin solution to provide a PEG solution having a final PEG concentration of from about 1% to about 5% (wt/vol). The term "% (wt/vol)" as used herein means the weight of material added per 100 ml of starting volume of solution. The percentages referred to herein are all weight per volume unless otherwise indicated. Preferably, the PEG is added in the form of a solution prepared by dissolving the PEG in distilled water that contains a citrate salt (such as sodium citrate). In one exemplary embodiment, the aqueous PEG solution, added to the cryoprecipitate/heparin solution, contains about 31.5% PEG, 0.22% sodium citrate dihydrate and 0.08% citric acid monohydrate at a pH of 6.2. The pH of the PEG solution is adjusted to between 5.5 to 7.1 with an acid such as dilute acetic acid. In one exemplary embodiment, the pH is about 6.3. The pH-adjusted PEG solution is mixed for approximately 15 minutes, at a temperature of from 15° C. to 35° C. In one embodiment, the temperature is about 27° C.

The addition of PEG (1% to 5%), and preferably 3% to 5%, to form the PEG solution results in precipitation of various proteins such as fibronectin and fibrinogen, leaving Factor VIII complex in solution. The fibronectin and other precipitated proteins, i.e., the PEG precipitate, are separated from the Factor VIII complex-containing solution (the PEG supernatant) by centrifugation. The PEG supernatant, i.e., the Factor VIII complex containing impure protein fraction, is recovered and processed further, in accordance with the process of this invention, to purify Factor VIII complex.

In an exemplary embodiment of practice of this invention, the Factor VIII complex production process includes steps for inactivating viruses that may be present in such blood products, e.g., hepatitis B virus, hepatitis non-A/non-B virus, HTLV III (AIDS virus), Cytomegalovirus, Epstein-Barr virus, and the like. In one embodiment, a solution comprising both an organic solvent and a detergent is added to the PEG supernatant to inactivate virus that may be present. The amount of organic solvent and detergent added preferably results in a solution containing about 0.3% organic solvent and about 1% detergent. Detergents useful in practice of principles of the invention are a detergent sold under the trademark "TWEEN-80" by Fisher Scientific of Springfield, New Jersey, or a detergent sold under the trademark "TRITON X-100," by Aldrich Company of Milwaukee, Wis. Useful organic solvents are tri-n-butylphosphate (TNBP) and ethyl ether, and the like. The solution is incubated for about 6 hours, at a temperature of from about 24° C. to about 30° C. Inactivation of virus using organic solvent/detergent mixture is described in Neurath et al. U.S. Pat. No. 4,540,573, which issued on Sep. 10, 1985 and which is incorporated herein by this reference.

The viral inactivated PEG supernatant solution, i.e., the Factor VIII complex containing impure protein fraction, is clarified by filtration and then further processed, for purification of Factor VIII complex, by affinity chromatography.

Preparation of Heparin Coupled Chromatographic Medium

Preparation of the heparin coupled chromatographic medium is achieved in accordance with this invention by coupling heparin or heparin sulfate to an activated resin. Activated resins useful in the practice of this invention include, but are not limited to, cyanogen bromide-activated agarose, N-hydroxy succinimide-activated agarose, aldehyde-activated agarose, cyanogen bromide-activated sepharose, cyanogen bromide-activated silica, and the like.

In one exemplary embodiment of preparing a heparin coupled chromatographic medium, heparin is bound to an activated aldehyde-agarose resin supplied by Sterogene Biochemicals of San Gabriel, California, under the trademark "ACTIGEL-A." In this embodiment, the ACTIGEL-A is washed and equilibrated in 3 volumes of a buffer, such as phosphate, acetate or borate buffers, at concentrations of about 0.1 molar (M), and at a pH of from about 6.5 to about 7.5. A coupling mixture of heparin in a buffer containing about 0.1M phosphate, acetate, or borate with about 0.1M sodium cyanoborohydride (NaCNBH$_3$), at a pH of from about 6.5 to about 7.5, is added to an equal volume of washed ACTIGEL-A resin and incubated for 12 to 20 hours at about 4° C. to about 30° C. with constant agitation on a mechanical mixer, such as a Labquake rotary tumbler supplied by Scientific Products of Irvine, Calif. After coupling, the mixture is filtered in a buchner funnel, using a medium-gauge, scintered-glass filter, and the retentate, i.e., the heparin coupled/ACTIGEL-A chromatographic medium, is washed by pouring several volumes of a solution comprising about 0.1M phosphate, acetate, or borate buffer, at about pH 6.5 to 7.5, containing 0.5M to 1M NaCl, through the retentate while in place on the buchner funnel. The washed heparin coupled chromatographic medium is then incubated at 4° C. to 30° C. in about 0.1M ethanolamine at about pH 6.5 to 7.5 for about two hours to deactivate any unreacted aldehyde groups. The heparin coupled chromatographic medium is filtered in a buchner funnel, using a medium-gauge, scintered-glass filter, and then washed by pouring several volumes of a solution containing about 1M NaCl through the heparin coupled chromatographic medium while in place on the buchner funnel. Finally, the medium is washed with a buffer, such as a phosphate buffer, at a concentration of about 0.1M, at about pH 6.5 to 7.5. The heparin coupled chromatographic medium is then stored refrigerated at about 4° C. to 10 C in about 0.1M phosphate buffer, pH 6.5 to 7.5, with about 0.01M sodium azide or other bactericide added as a preservative.

The amount of heparin used in the coupling reactions is preferably from about 250 to about 2000 units of heparin per ml of ACTIGEL-A, and is more preferably about 1000 units of heparin per ml of ACTIGEL-A, since this concentration gives optimal binding of Factor VIII complex. At concentrations below about 1000 units per ml, there are undesirably high concentrations of Factor VIII complex found in the chromatography effluent. At concentrations greater than 1000 units of heparin per ml, there is no increase in the amount of Factor VIII complex bound and, therefore, the additional heparin would add unnecessarily to the cost of the process.

Preparation of the Chromatography Column

In one embodiment of practice of the process of the invention, chromatographic columns such as those supplied by Amicon Corporation of Danvers, Mass., are used. The column includes an elongated hollow container having an outlet at its bottom The heparin coupled chromatographic medium prepared as described above is decanted from the sodium azide preservative solution, in which it is stored, and washed with a buffer, such as imidazole buffer, containing from about 0.01M to about 0.05M imidazole, at a pH of about 6.5 to 7.5. The heparin coupled chromatographic medium is slurried with a sufficient volume of buffer, such as 0.01M to 0.05M imidazole buffer, pH 6.5 to 7.5, so that the slurry volume does not exceed the total column volume, and the slurry is not so thick as to retain air bubbles. The bottom of the column is filled with from about 1 to about 3 centimeters of a solution comprising a buffer, such as 0.02M to 0.05 imidazole buffer, at about pH 6.5 to 7.5, containing about 0.1M to 0.15M of a salt, such as NaCl, LiCl, or KCl, at the temperature at which the column is to be run. The slurried chromatographic medium is then packed into the column by pouring it down the side wall, to provide a heparin coupled chromatography column useful in the practice of this invention to separate Factor VIII complex from the impure protein fraction containing Factor VIII complex.

If desired, in accordance with the techniques of this invention for separation of Factor VIII complex from the impure protein fraction, the heparin coupled chromatographic medium can be used in a batch, rather than a column, process. In the batch process, the heparin coupled chromatographic medium prepared as described above is decanted from the sodium azide solution in which it is stored and is washed with a buffer, such as imidazole buffer, at a concentration of about 0.01M to about 0.05M at a pH of about 6.5 to 7.5. The buffer solution is decanted, and the washed heparin coupled chromatographic medium is added directly to the Factor VIII complex containing impure protein fraction.

Separation of Factor VIII Complex by Affinity Column Chromatography

In an exemplary embodiment of the practice of this invention, Factor VIII complex solution from the viral inactivation step (the Factor VIII complex containing impure protein fraction) is applied to the chromatography column containing the heparin coupled chromatographic medium by pouring the solution through the column. The flow rate of the column is about 0.35 ml per min. for a small (about 5 ml) column to about 2 ml per min. for a large (about 50 ml) column. As the impure protein fraction flows through the column, Factor VIII complex binds to the heparin ligand on the heparin coupled chromatographic medium, while other proteins pass through the chromatographic medium in the column and flow from the column as effluent. Preferably, no more that about 20 units of Factor VIII:C activity are applied to the column per ml of heparin coupled chromatography medium in the column when, as in one exemplary embodiment, 1000 units of heparin are bound per ml of activated resin. When greater than about 20 units of Factor VIII:C activity are added per ml of heparin coupled chromatographic medium, the excess Factor VIII complex is not bound but is instead washed through the column into the column effluent. If less than about 20 units of Factor VIII:C activity per ml are added, the maximum binding capacity of the heparin coupled chromatographic medium (at 1000 units of heparin per ml of activated resin) is not being used.

The heparin coupled chromatographic medium with Factor VIII complex bound to it, is washed to remove all unbound proteins. In one exemplary embodiment, the washing is effected by applying about 5 to 10 volumes of a solution comprising about 0.01 to 0.05M buffer, such as imidazole buffer, pH 6.5 to 7.5, containing about 0.1M to 0.15M of a salt solution, such as LiCl, NaCl, or KCl, and the effluent from the column is collected. Preferably, the solution comprises 0.02M imidazole buffer at a pH of 6.8 containing 0.15M NaCl. The Factor VIII complex remains bound to the chromatographic medium throughout the wash procedure.

Factor VIII complex is eluted from the column, i.e., from the heparin coupled chromatographic medium, by applying to the column, a buffered aqueous solution incorporating calcium, magnesium, strontium, or other divalent metal ion salt, such as $CaCl_2$, $MgCl_2$, $SrCl_2$ or the like. Preferably, the eluting agent is $CaCl_2$ at a concentration of from about 0.01M to about 0.3M. More preferably, the $CaCl_2$ is at a concentration of from about 0.05M to about 0.2M, and most preferably, the $CaCl_2$ is at a concentration of about 0.1M. In an exemplary embodiment, the buffer comprises imidazole at a concentration of about 0.01M to about 0.05M, and the solution is at a pH of from about 6.5 to about 7.5. The column is washed with the buffered $CaCl_2$ solution until all the Factor VIII complex is washed from the column. Typically, from about 2 to about 4 column volumes of the buffered $CaCl_2$ solution are applied to the column to elute Factor VIII complex. When the concentration of $CaCl_2$ is less than about 0.05M, less than a desirable amount of Factor VIII complex is eluted from the heparin coupled chromatographic medium. When the concentration of $CaCl_2$ is greater than about 0.2M, unwanted proteins are eluted along with the Factor VIII complex, thereby reducing the specific activity of Factor VIII complex in the final product. Also, salt concentrations greater than 0.2M can lead to dissociation of the Factor VIII complex, which results in the Factor VIII being less stable. Preferably, the concentration of $CaCl_2$ is about 0.1M, to maximize the amount of Factor VIII complex eluted but to minimize elution of unwanted proteins and dissociation of the Factor VIII complex.

The Factor VIII complex eluted from the heparin coupled chromatographic medium is concentrated by ultrafiltration, approximately 20-fold, and the calcium concentration is reduced to from about 0.002M to about 0.005M. A histidine buffer and a glycine stabilizer are added to the ultrafiltered Factor VIII complex solution to provide histidine at a concentration of about 0.025M and glycine at a concentration of about 0.28M, and the pH is adjusted, using from about 1M to about 6M HCl, to approximately 7.3. The solution is then divided among separate vials, with each vial containing a desired number of units of Factor VIII:C activity. The solutions are then lyophilized to provide separate vials of purified Factor VIII complex concentrate.

Separation of Factor VIII by Affinity Chromatography in a Batch Process

In an exemplary embodiment of the practice of this invention, Factor VIII complex solution from the viral inactivation step (the Factor VIII complex containing impure protein fraction) is applied directly to the washed heparin coupled chromatographic medium and mixed for about 30 min. to about 45 min. for batch processing. During this time, the Factor VIII complex binds to the heparin ligand on the chromatographic medium, leaving a supernatant containing proteins other than Factor VIII complex in solution. The chromatographic medium is removed by decanting the supernatant, and the medium is then washed to remove unbound proteins. In one exemplary embodiment, the washing is effected by resuspending the Factor VIII complex bound heparin coupled chromatographic medium in about 5 to 10 volumes of a solution comprising about 0.01 to 0.05M buffer, such as imidazole buffer, pH 6.5 to 7.5, containing a salt solution, such as LiCl, NaCl, or KCl, at a concentration of about 0.1M to about 0.15M. Preferably, the solution comprises 0.02M imidazole buffer at a pH of 6.8 containing 0.15M NaCl. The Factor VIII complex bound heparin coupled chromatographic medium is removed from the wash solution by decanting the supernatant, i.e., the wash solution. The Factor VIII complex remains bound to the heparin coupled chromatographic medium throughout the wash procedure.

Factor VIII complex is eluted from the heparin coupled chromatographic medium by resuspending the chromatographic medium in about 2 to about 4 volumes of a buffered solution comprising $CaCl_2$ as the eluting agent. In an exemplary embodiment, the eluting agent is $CaCl_2$ at a concentration of from about 0.01 to about 0.3M in a buffer comprising imidazole at a concentration of about 0.01M to about 0.05M, and at a pH of from about 6.5 to about 7.5. Preferably, the $CaCl_2$ eluting agent is at a concentration of from about 0.05M to about 0.2M, and most preferably, the concentration of $CaCl_2$ is about 0.1M. After the elution step, the heparin coupled chromatographic medium is removed from the $CaCl_2$ solution by decanting the supernatant, which contains the eluted Factor VIII complex. The Factor VIII complex containing supernatant eluted from the heparin coupled chromatographic medium is then concentrated by ultrafiltration, approximately 20-fold, and the calcium concentration is reduced to from about 0.002M to about 0.005M. A histidine buffer and a glycine stabilizer are added to the ultrafiltered Factor VIII complex solution to provide histidine at a concentration of about 0.025M and glycine at a concentration of about 0.28M, and the pH is adjusted, using from about 1M to about 6M HCl, to approximately 7.3. The solution is then divided among separate vials, with each vial containing a desired number of units of Factor VIII:C activity. The solutions are then lyophilized to provide separate vials of purified Factor VIII complex concentrate.

EXAMPLE 1

Preparation of an Impure Protein Fraction Containing Factor VIII

Forty grams of cryoprecipitate was dissolved in 120 ml of distilled water containing about 80 units of heparin per ml of water. The heparin solution was mixed at a temperature of about 30° C. until the cryoprecipitate was completely dissolved (approximately 10 minutes) to provide a cryoprecipitate/heparin solution. After the cryoprecipitate was dissolved, the pH of the cryoprecipitate/heparin solution was adjusted to about 7 using 0.1M HCl, and the solution was stirred for an additional 20 to 30 minutes.

An aqueous PEG solution containing about 31.5% PEG, 0.22% sodium citrate dihydrate, and 0.08% citric acid monohydrate at a pH of 6.2, was then added to the cryoprecipitate/heparin solution to give a final concentration of 3.5% PEG. The pH of the PEG/cryoprecipitate/heparin solution was adjusted to about 6.3 with dilute acetic acid. The pH-adjusted solution was mixed for approximately 15 minutes, at a temperature of about 27° C. The addition of PEG resulted in precipitation of various contaminating proteins from the Factor VIII complex which remained in solution.

The PEG precipitate was separated from the Factor VIII complex-containing supernatant solution by centrifugation. The supernatant, i.e., the Factor VIII complex containing impure protein fraction, was recovered. The supernatant was then treated to inactivate viruses, that may be present in the blood products, by the addition of a solution containing about 0.3% tri-n-butylphosphate and about 1% TWEEN-80 and incubating at 25° C. for about 30 min.

The viral-inactivated supernatant solution, i.e., the viral-inactivated Factor VIII complex containing impure protein fraction, was clarified by filtration and then recovered for further purification of Factor VIII complex, by affinity chromatography on a heparin coupled chromatographic medium.

EXAMPLE 2

Preparation of Heparin Coupled Chromatographic Medium and Test for Factor VIII Complex Binding Capacity One hundred grams of ACTIGEL-A was washed and equilibrated in 1000 ml of 0.1M phosphate buffer, pH 6.8. A coupling mixture containing 50,000 units of heparin in 0.1M phosphate buffer, pH 6.8, with 0.1M NaCNBH$_3$, to give a final concentration of 250 units of heparin per ml of ACTIGEL-A, was added to an equal volume of washed ACTIGEL-A and incubated for 18 hours at room temperature with constant rotation on a Labquake rotary tumbler. The coupling mixture was then filtered in a buchner funnel, using a medium-gauge, scintered-glass filter. The retentate, i.e., the heparin coupled/ACTIGEL-A chromatographic medium, was washed in several volumes of a solution comprising 0.1M phosphate buffer, pH 6.8, and 0.5M NaCl. The washed heparin coupled ACTIGEL-A medium was then incubated at 23° C. in 0.1M ethanolamine, at pH 6.8, for 2 hours to deactivate the unreacted aldehyde groups. Finally, the heparin coupled chromatographic medium was filtered in a buchner funnel, using a medium-gauge, scintered-glass filter, and then washed with 1M NaCl, then with 0.1M imidazole buffer, pH 6.8, containing 0.15M NaCl, and tested for its ability to bind Factor VIII complex.

To test for Factor VIII complex binding, an impure protein fraction containing 100 units of Factor VIII:C activity in a Factor VIII complex, provided by a process, such as the process described in Example 1, was added batchwise to a 5 ml sample of heparin coupled chromatographic medium and mixed for 30 minutes. The supernatant was then decanted from the chromatographic medium, and the medium washed by resuspending it in 50 ml of 0.02M imidazole buffer, pH 6.8, containing 0.15M NaCl. After the chromatographic medium settled, the wash solution was decanted. The decanted supernatant and wash solution were combined to form the effluent sample. After all unbound proteins were washed from the medium, as determined by the adsorbance of the effluent material using a spectrophotometer, Model No. 2600, supplied by Gilford Co. of Walnut Creek, Calif., the bound Factor VIII complex was eluted by resuspending the medium in 0.02M imidazole buffer, pH 6.8, containing 0.1M CaCl$_2$. After the medium settled, the supernatant was decanted. This process was repeated until no additional protein was eluted from the medium. These samples were combined to form the eluate sample. The eluate and effluent samples were assayed for Factor VIII:C blood-clotting activity using a clotting machine supplied by General Diagnostics of Durham, N.C., under the trade name "COAG-A-MATE XC." Factor VIII:C activity in the effluent, i.e., the Factor VIII:C which did not bind to the heparin coupled chromatographic medium, was found to be 45 units. The Factor VIII:C activity found in the eluate sample, i.e., the Factor VIII:C that bound to the heparin coupled chromatographic medium and subsequently eluted, was 20 units.

EXAMPLE 3

The procedure of Example 2 was repeated, except that 100,000 units of heparin were added to provide a heparin coupled chromatographic medium with a final concentration of 500 units of heparin per ml of ACTIGEL-A. Factor VIII:C activity in the effluent and eluate samples were found to be 16 units and 48 units, respectively.

EXAMPLE 4

The procedure of Example 2 was repeated, except that 200,000 units of heparin were added to provide a heparin coupled chromatographic medium with a final concentration of 1000 units of heparin per ml of ACTIGEL-A. Factor VIII:C activity in the effluent and eluate samples were found to be 6 units and 78 units, respectively.

EXAMPLE 5

The procedure of Example 2 was repeated, except that 400,000 units of heparin was added to provide a heparin coupled chromatographic medium with a final concentration of 2000 units of heparin per ml of ACTIGEL-A. Factor VIII:C activity in the effluent and eluate samples were found to be 3 units and 65 units, respectively.

Table 1 lists the results of Examples 2-5.

TABLE 1

| Example | Units of Heparin per ml of ACTIGEL-A | Factor VIII:C Activity in Eluate | Factor VIII:C Activity in Effluent |
| --- | --- | --- | --- |
| 2 | 250 | 20 | 48 |
| 3 | 500 | 48 | 16 |
| 4 | 1000 | 78 | 6 |
| 5 | 2000 | 65 | 3 |

As shown in Examples 2–5, the optimum binding of Factor VIII complex when an impure protein solution containing 100 units of Factor VIII:C was applied to 5 ml of the heparin coupled ACTIGEL-A chromatographic medium, was achieved when the activated resin contained 1000 units of heparin per ml of resin.

EXAMPLE 6

Purification of Factor VIII Complex by Heparin Affinity Chromatography

Five ml of heparin coupled/ACTIGEL-A chromatographic medium, prepared in accordance with the procedure of Example 4, was packed into a column washed with 50 ml of 0.02M imidazole buffer, pH 6.8, with 0.15M NaCl. An impure protein faction, prepared by a process, such as the process described in Example 1, containing a total of 18 units of Factor VIII:C activity was applied to the column, i.e., the heparin coupled chromatographic medium packed into the column, and the flow rate of the column was maintained at 0.35 ml per min. The column effluent was collected and the column was washed with 50 ml of 0.02M imidazole buffer, pH 6.8, containing 0.15M NaCl. Elution of Factor VIII complex was achieved with 15 ml of 0.1M $CaCl_2$ in 0.02M imidazole buffer, pH 6.8. All effluent and eluate samples were assayed for Factor VIII:C blood-clotting activity using a COAG-A-MATE XC clotting machine.

Of the 18 units of Factor VIII:C activity applied to the column, 15.9 units were eluted with 0.1M $CaCl_2$. The Factor VIII:C recovered had a specific activity of 57.7 units/mg. In this example, and in Examples 7, 8, and 9, "%" refers to the proportion of Factor VIII:C activity recovered in the sample as compared to the total Factor VIII:C activity bound to the heparin coupled chromatographic medium.

EXAMPLE 7

The procedure of Example 6 was repeated, except that an impure protein fraction containing a total of 19.8 units of Factor VIII:C activity was applied to the 5-ml heparin affinity chromatography column. Of the 19.8 units of Factor VIII:C activity applied to the column, 12.8 were eluted with 0.1M $CaCl_2$. The Factor VIII complex recovered had a specific activity of 49.2 units of Factor VIII:C/mg.

Table 2 lists the results of Examples 6 and 7.

TABLE 2

| Factor VIII:C Activity | Example 6 | Example 7 |
| --- | --- | --- |
| Applied to Column (units) | 18.0 | 19.8 |
| Eluate (units) | 15.9 | 12.8 |
| Specific activity (units/mg) | 57.7 | 49.2 |

EXAMPLE 8

The procedure of Example 6 was repeated, except that a column containing 50 ml of heparin coupled/ACTIGEL-A chromatographic medium, prepared in accordance with Example 4, was used. An impure protein fraction, prepared by a process, such as the process described in Example 1, containing a total of 1004 units of Factor VIII:C activity was applied to the column, and the flow rate of the column was maintained at 2 ml per minute. Of the 1004 units of Factor VIII:C activity applied to the column, 398 units were eluted with 0.1M $CaCl_2$. The Factor VIII complex recovered had a specific activity of 66 units of Factor VIII:C activity/mg.

EXAMPLE 9

The procedure of Example 8 was repeated, except that an impure protein fraction containing 390 units of Factor VIII:C activity was applied to the heparin coupled chromatography column.

Of the 390 units of Factor VIII:C activity was applied to the column, 315 units were eluted with 0.1M $CaCl_2$. The Factor VIII complex recovered had a specific activity of 50 units of Factor VIII:C activity/mg.

Table 3 lists the results of Examples 8 and 9.

TABLE 3

| Factor VIII:C Activity | Example 8 | Example 9 |
| --- | --- | --- |
| Applied to Column (units) | 1004 | 390 |
| Eluate (units) | 398 | 315 |
| Specific activity (units/mg) | 66 | 50 |

As shown in Examples 6–9, the average specific activity of the eluted Factor VIII complex was 55.73 units of Factor VIII:C activity/mg.

EXAMPLE 10

Comparison of Affinity Elution With Ionic Elution

Five ml of a heparin coupled/ACTIGEL-A chromatographic medium, prepared in accordance with the procedure of Example 4, having 1000 units of heparin bound per ml of ACTIGEL-A, was packed into a column and washed with 50 ml of 0.02M imidazole buffer, pH 6.8, with 0.15M NaCl. In numerous experiments, which have been combined in this example, impure protein fractions, prepared by a process, such as the process described in Example 1, and containing from 15 to 42 units of Factor VIII:C activity were separately applied to the column. The flow rate of the column was maintained at 0.4 ml/min. For each separate "column run," the column effluent was collected, and the column was washed until all unbound proteins were eluted from the heparin coupled chromatographic medium with 50 ml of 0.02M imidazole buffer, pH 6.8, containing 0.15M NaCl. Factor VIII complex was then eluted with 15 ml of 0.1M $CaCl_2$ in 0.02M imidazole buffer, pH 6.8. The effluent and eluate samples were assayed for Factor VIII:C activity using a COAG-A-MATE XC clotting machine. The specific activity of the Factor VIII complex recovered in these experiments ranged from 30 to 60 units of Factor VIII:C activity/mg.

EXAMPLE 11

The procedure of Example 10 was repeated, except that elution of Factor VIII complex was achieved with 0.5M NaCl in place of 0.1M $CaCl_2$. The specific activity of the Factor VIII complex recovered in these experiments ranged from 5 to 10 units of Factor VIII:C activity/mg.

Table 4 represents the data collected from numerous experiments and reflects the results of Examples 10 and 11.

TABLE 4

| Factor VIII:C Activity | Example 10 | Example 11 |
| --- | --- | --- |
| Applied to Column (units) | 15 to 42 | 15 to 42 |
| Eluate Factor VIII:C Activity (units/ml) | 1.5 to 2.5 | 1.5 to 2 |
| Eluate Protein Content (mg/ml) | 0.04 to 0.05 | 0.2 to 0.3 |
| Specific Activity (units/mg) | 30 to 60 | 5 to 10 |

As shown in Examples 10 and 11, the specific activity of the Factor VIII:C recovered by affinity elution with 0.1M $CaCl_2$ is higher than that recovered by ionic elution with 0.5M NaCl, due to the elution of additional contaminating or inactive protein, with 0.5M NaCl.

EXAMPLE 12

Optimization of Factor VIII Complex Elution from the Heparin Coupled Chromatographic Medium with $CaCl_2$ Five ml of the heparin coupled chromatographic medium having 1000 units of heparin bound per ml of ACTIGEL-A provided in accordance with the process of Example 4, was packed into a column and washed with 50 ml of a solution comprising 0.02M imidazole, pH 6.8, and 0.15M NaCl. An impure protein fraction containing Factor VIII:C in a Factor VIII complex provided by a process, such as the process described in Example 1, containing a total of 62.4 units of Factor VIII:C activity, was applied to the column containing the heparin coupled chromatographic medium. The column effluent was collected, and the heparin coupled chromatographic medium was washed with 50 ml of 0.02M imidazole buffer, pH 6.8, containing 0.15M NaCl. The effluent and wash, i.e., the column effluent, were combined. Factor VIII complex was then eluted with 10 ml of 0.05M $CaCl_2$ in 0.02M imidazole buffer, pH 6.8. The column effluent and the eluate samples were assayed for Factor VIII:C blood-clotting activity using a COAG-A-MATE XC clotting machine. Factor VIII:C activity in the effluent and the eluate samples was found to be 18.9 units and 26.2 units, respectively. The specific activity of the eluted Factor VIII complex was 50.4 units of Factor VIII:C activity/mg.

EXAMPLE 13

The procedure of Example 12 was repeated, except that elution of Factor VIII complex activity was achieved using a solution having a $CaCl_2$ concentration of 0.1M. The Factor VIII:C activity in the column effluent and the eluate samples was 14.1 units and 36.8 units, respectively. The specific activity of the eluted Factor VIII:C was 34.5 units/mg.

EXAMPLE 14

The procedure of Example 12 was repeated, except that elution of Factor VIII complex activity was achieved using a solution having a $CaCl_2$ concentration of 0.2M. The Factor VIII:C activity in the column effluent and the eluate samples was 19.4 units and 36.3 units, respectively. The specific activity of the eluted Factor VIII:C was 30.6 units/mg.

As is shown in Examples 12-14, the number of units of Factor VIII:C activity in the eluate is less when the eluting solution contains 0.05M $CaCl_2$ than when the $CaCl_2$ concentration is high, such as at 0.1M or 0.2M. The specific activity of the Factor VIII:C in the eluted Factor VIII complex is less when the eluting solution contains 0.2M $CaCl_2$ than when the $CaCl_2$ concentration is lower, such as at 0.1M or 0.05M.

EXAMPLE 15

Properties of Factor VIII Complex Purified by Heparin Affinity Chromatography

Fifty ml of heparin coupled/ACTIGEL-A chromatographic medium, prepared in accordance with the procedure of Example 4, was packed into a column and washed with 500 ml of 0.02M imidazole buffer, pH 6.8, with 0.15M NaCl. An impure protein fraction, prepared by a process, such as the process described in Example 1, containing a total of 390 units of Factor VIII:C activity was applied to the column, i.e., to the heparin coupled chromatographic medium packed into the column, and the flow rate of the column was maintained at 2 ml per min. The column effluent was collected, and the column was washed with 500 ml of 0.02M imidazole buffer, pH 6.8, containing 0.15M NaCl. Elution of Factor VIII complex was achieved with 100 ml of 0.1M $CaCl_2$ in 0.02M imidazole buffer, pH 6.8.

The Factor VIII complex eluted from the heparin coupled chromatographic medium was concentrated by ultrafiltration, approximately 20-fold, and the calcium concentration was reduced to from about 0.002M to about 0.005M. A histidine buffer and a glycine stabilizer were added to the ultrafiltered Factor VIII complex solution to provide histidine at a concentration of about 0.025M and glycine at a concentration of about 0 28M, and the pH was adjusted, using from about 1M to about 6M HCl, to approximately 7.3. The solution was then divided among separate vials, with each vial containing a desired number of units of Factor VIII:C activity. The separate vials were then frozen at $-70°$ C. and lyophilized.

The Factor VIII complex concentrate was reconstituted by the addition of 10 ml of water and mixing for one 1 min. The reconstituted Factor VIII complex was then assayed for Factor VIII:C blood-clotting activity using a COAG-A-MATE XC clotting machine, and for Factor VIII:R activity using a Ristocetin cofactor assay kit supplied under the trade name HELENA by Helena Laboratories of Beaumont, Tex. A unit of Factor VIII:R activity is defined as the amount of Factor VIII:R in one ml of plasma.

A vial of reconstituted Factor VIII complex contained 42 units/ml of Factor VIII:C activity and 64 units/ml of Factor VIII:R activity. The specific activity of Factor VIII:C was 35 units/mg and of Factor VIII:R, was 53 units/mg. The protein concentration of the reconstituted Factor VIII complex was 1.2 mg/ml.

The above descriptions of exemplary embodiments of processes for producing Factor VIII complex concentrate are for illustrative purposes. Because of variations which will be apparent to those skilled in the art, the present invention is not intended to be limited to the particular embodiments described above. The scope of the invention is defined by the following claims.

What is claimed is:

1. A process for separating Factor VIII complex from an impure protein fraction containing Factor VIII complex, comprising the steps of:
   providing an aqueous solution of the impure protein fraction containing Factor VIII complex;
   applying the impure protein fraction solution to a heparin coupled chromatographic medium;

binding Factor VIII complex to the heparin; and eluting the Factor VIII complex from the chromatographic medium using an aqueous solution containing $CaCl_2$ as the eluting agent, and recovering Factor VIII complex from the eluate.

2. The process of claim 1 wherein the $CaCl_2$ is in the solution at a concentration of from about 0.01M to about 0.3M.

3. The process of claim 1 wherein the $CaCl_2$ is in the solution at a concentration of from about 0.05M to about 0.2M.

4. The process of claim 1 wherein the concentration of $CaCl_2$ is greater than about 0.05M.

5. The process of claim 2 wherein the concentration of $CaCl_2$ is about 0.1M.

6. The process of claim 1 wherein the aqueous $CaCl_2$ solution has a pH of from about 6.5 to 7.5 and includes an imidazole buffer at a concentration of from about 0.01M to about 0.05M.

7. The process of claim 6 wherein the pH is maintained at about 6.8, and the imidazole buffer is at a concentration of about 0.02M.

8. The process of claim 1 wherein the impure protein fraction containing Factor VIII complex is derived from cryoprecipitate.

9. The process of claim 1 wherein the impure protein fraction is applied to the heparin coupled chromatographic medium in a batch process.

10. A process for separating Factor VIII complex from an impure protein fraction containing Factor VIII complex, comprising the steps of:

providing an aqueous solution of an impure protein fraction containing Factor VIII complex;

applying the impure protein fraction solution to a chromatographic column containing a heparin coupled chromatographic medium;

binding Factor VIII complex to the heparin ligand on the chromatographic medium; and eluting the Factor VIII complex from the chromatographic medium using an aqueous solution containing $CaCl_2$ as the eluting agent, and recovering Factor VIII complex from the eluate.

11. The process of claim 10 wherein the concentration of $CaCl_2$ in the aqueous solution is from about 0.05M to about 0.2M.

12. The process of claim 10 wherein concentration of $CaCl_2$ in the aqueous solution is about 0.1M.

13. The process of claim 10 wherein the aqueous $CaCl_2$ solution has a pH of from about 6.5 to 7.5 and includes an imidazole buffer at a concentration of from about 0.01M to about 0.05M.

14. The process of claim 13 wherein the pH is maintained at about 6.8, and the imidazole buffer is at a concentration of about 0.02M.

15. The process of claim 10 wherein the impure protein fraction containing Factor VIII is derived from cryoprecipitate.

* * * * *

UNITED STATES PATENT AND TRADEMARK OFFICE
CERTIFICATE OF CORRECTION

PATENT NO. : 5,110,907
DATED : May 5, 1992
INVENTOR(S) : David P. Kosow, et al.

It is certified that error appears in the above-identified patent and that said Letters Patent is hereby corrected as shown below:

Column 3, Line 43, change "5to" to -- 5 to --;

Column 5, Line 54, after "funnel" insert a period;

Column 5, Line 67, change "10C" to -- 10°C --;

Column 6, Line 22, after "bottom" insert a period;

Column 9, Line 17, change "022%" to -- 0.22% --;

Column 10, Line 23, change "68" to -- 6.8 --;

Column 14, line 31, change "028" to -- 0.28 --;

Column 14, Line 40, change "1" to -- (1) --.

Signed and Sealed this

Seventh Day of December, 1993

Attest:

BRUCE LEHMAN

Attesting Officer

Commissioner of Patents and Trademarks